United States Patent [19]

Parth et al.

[11] Patent Number: 4,771,642
[45] Date of Patent: Sep. 20, 1988

[54] SOLIDS SAMPLER

[75] Inventors: William H. Parth, Saginaw; Charles J. Myers, Midland, both of Mich.

[73] Assignee: The Dow Chemical Company, Midland, Mich.

[21] Appl. No.: 76,247

[22] Filed: Jul. 21, 1987

[51] Int. Cl.$^4$ .......................... G01N 1/20; G01N 1/08
[52] U.S. Cl. .............. 73/863.52; 73/863.21; 73/863.54; 73/863.81; 73/863.85
[58] Field of Search .............. 73/863.81–863.86, 73/863.43, 863.52, 863.53, 863.54, 863.58, 863.21, 863.22

[56] References Cited

U.S. PATENT DOCUMENTS

| | | | |
|---|---|---|---|
| 3,735,641 | 5/1973 | Bink et al. | 73/863.43 |
| 4,024,765 | 5/1977 | Abonnenc | 73/863.83 |
| 4,399,710 | 8/1983 | Schneider | 73/863.83 |
| 4,426,888 | 1/1984 | Smith | 73/863.83 |
| 4,433,587 | 2/1984 | Risdal | 73/863.83 X |
| 4,625,570 | 12/1986 | Witherspoon et al. | 73/863.81 |

OTHER PUBLICATIONS

"Model 261 Automatic Solid Material Sampler," Sales Brochure by Anacon Inc; 3 pages, published by 10-2-3-1986.
Schematics of an Auto Sampler System, Drawing No. C-200674, dated 11-10-83; and a Sampler Assembly, Drawing No. C-200626, dated 6-11-83; each one sheet.

Primary Examiner—Tom Noland
Attorney, Agent, or Firm—Timothy S. Stevens; Edward E. Schilling

[57] ABSTRACT

Apparatus for collecting a sample of particulate matter from a pneumatic conveyer system. A sample cup is positioned in the stream of gas carrying the particulate matter with the opening of the cup facing the gas stream. A foreshortened hollow duct-shaped collector element is positioned above the cup and aligned therewith. The transverse interior dimensions of the cup and collector are about the same. This positioning of the collector allows the particulate sample to settle into the cup and substantially prevents the sample from being blown out of the cup by the stream of gas which can be a serious problem when the gas stream velocity is relatively high and the collector element is not used. If it is desired to remove the sample cup through an opening in the wall of the pneumatic conveyer, a shield is provided between the collector element and the wall to substantially prevent the sample from being blown out of the cup by the stream of gas as the cup is being withdrawn.

11 Claims, 2 Drawing Sheets

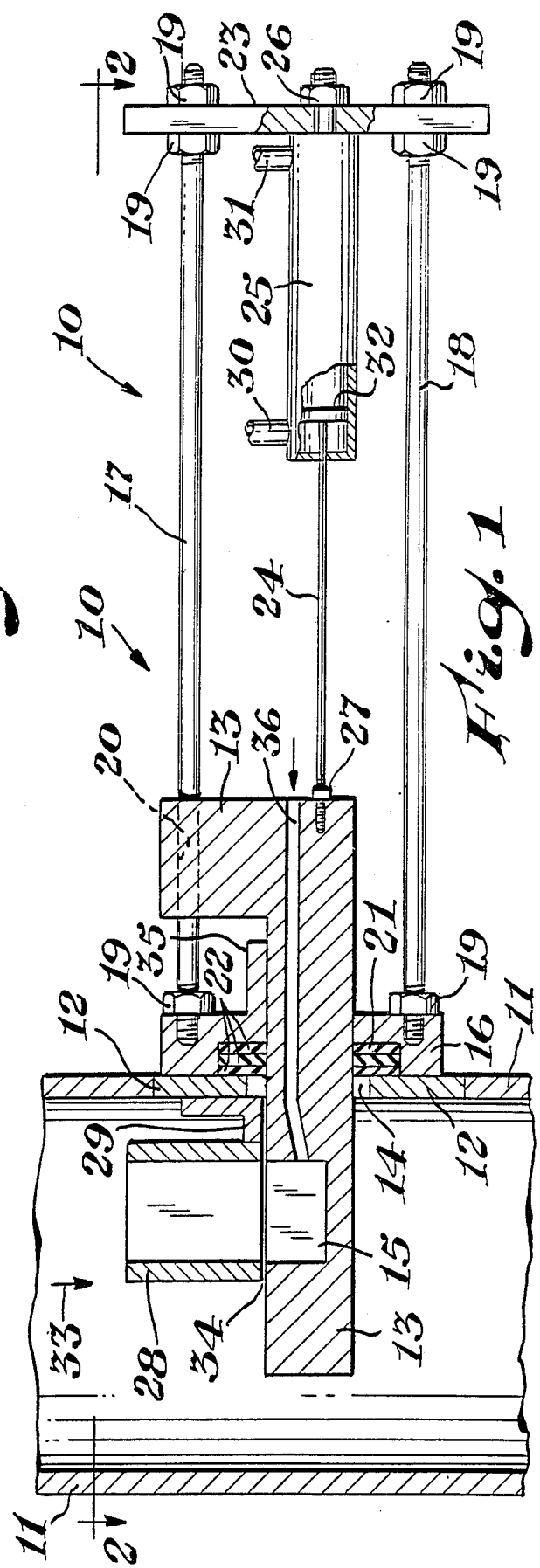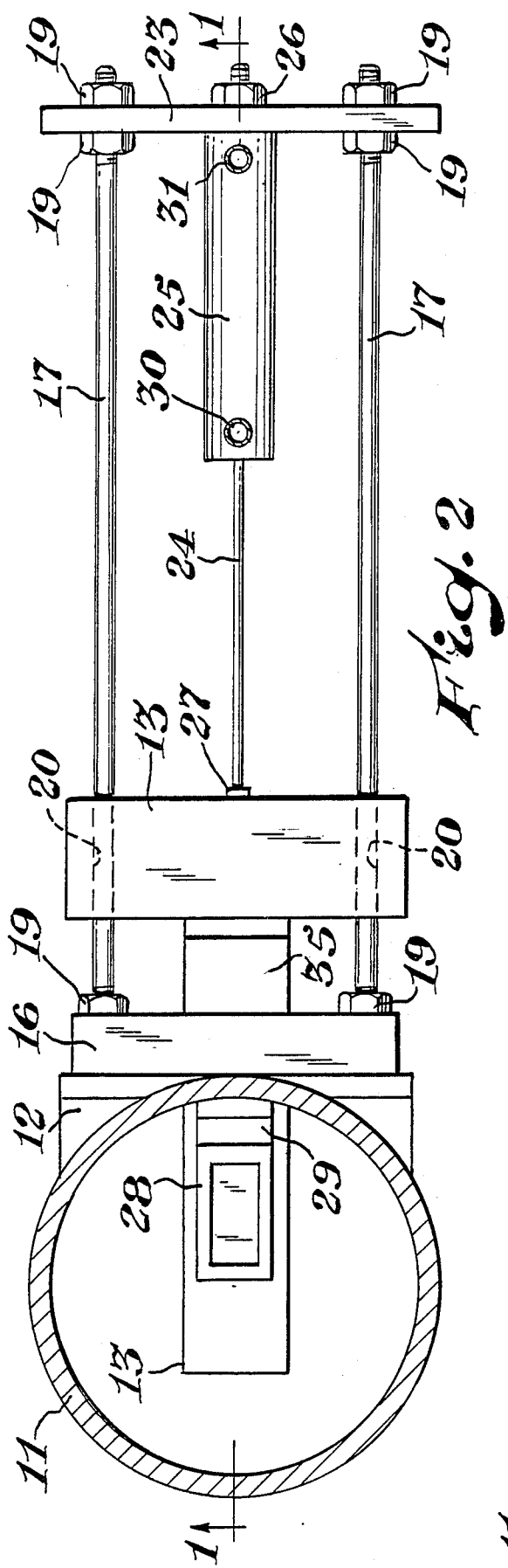

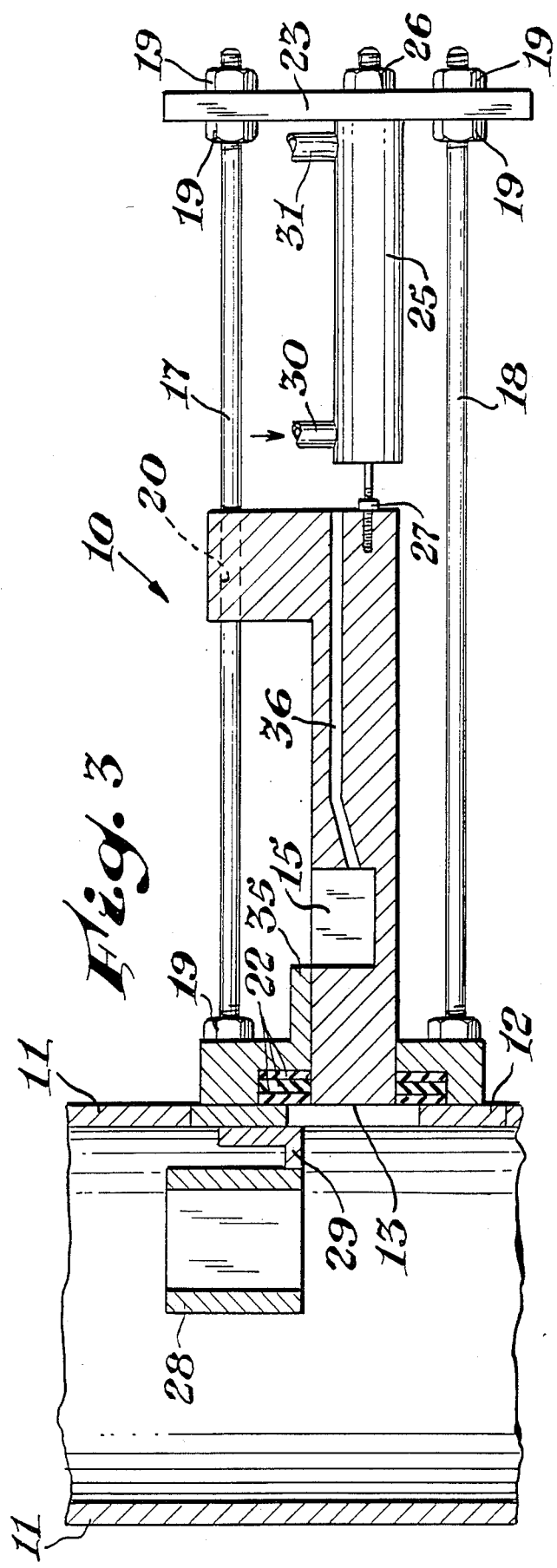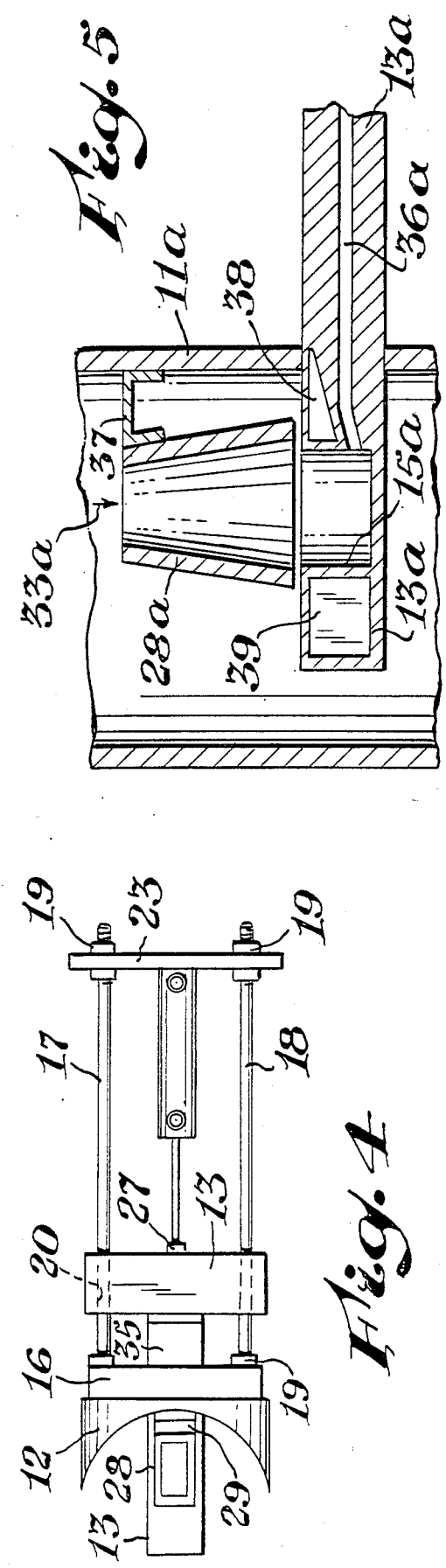

SOLIDS SAMPLER

FIELD OF THE INVENTION

The invention is in the field of apparatus for sampling pneumatically conveyed particulate solids.

BACKGROUND OF THE INVENTION

One means of conveying particulate solids is in a conduit along with a flowing stream of gas, usually air, i.e., pneumatically conveying the particulate solids. The particulate solids generally need to be conveyed between various stages of processing. For example, polymer resin beads are pneumatically conveyed. It may be desirable to sample the particulate solids being pneumatically conveyed so that a chemical or physical analysis can be made of the particulate solid. Several samplers have been developed for this purpose.

Witherspoon et al, in U.S. Pat. No. 4,625,570, describe a device for removing samples of solid particulate dropped through a vertical pipeline. The device includes a scoop, i.e., a sample cup which can be telescoped into the pipeline through a side mounting track, attached to a flange on the pipeline, to catch a sample of the solid particulate in the scoop, and then telescoped out of the pipeline into the mounting track. The mounting track has a lower discharge opening which registers with the scoop when the latter is rotated 180 degrees so that the sample can be dropped into a container. The inner end of the scoop is closed so that the pipeline remains closed during all phases of the sampling operation. The Witherspoon et al device is designed for gravity conveyed particulate solids and is hand operated.

The Anacon Model 261 Automatic Sampler also uses a sample cup mounted on a probe that can be inserted and withdrawn from the conduit by a pneumatic actuator. The sample cup is equipped with a false bottom that can be withdrawn by another pneumatic actuator. In operation, the cup is inserted into the conduit and filled with the particulate solid. Then the cup is withdrawn from the conduit and positioned over an analyzer that directs a beam of near-infrared light onto the sample in the cup and thereby determines the moisture content of the sample by analyzing the near-infrared light reflected from the sample. The cup is then reinserted into the conduit and the false bottom withdrawn to return the sample to the process stream. The false bottom is then returned to collect another sample. The Anacon device is designed for gravity or pneumatically conveyed particulate solids and is automatic in operation.

When the Anacon device is installed in a pneumatic conveyer, operating at an average air velocity of about 80 feet per second, to collect samples of polymer beads so that the moisture content of the beads can be determined, a serious problem occurs, i.e., little or no sample is collected in the cup. Apparently, the air velocity is so high that the sample is blown out of the cup preventing the accumulation of any appreciable amount. The present invention overcomes this problem.

SUMMARY OF THE INVENTION

The apparatus aspect of this invention is a solids sampler which will collect a sample of particulate solids from a gas stream flowing in a conduit, the sample being collected in a cup-like receptacle in combination with a hollow duct-shaped collector element positioned in the conduit with the opening thereof oriented to face upstream to the flow of gas within the conduit, effectively retaining the sample even when the gas stream is flowing at a relatively high velocity. The foreshortened hollow duct-shaped collector element is positioned adjacent the opening of the receptacle, substantially aligned therewith and having about the same interior transverse dimensions as the receptacle so as to lead particulate matter into the receptacle while substantially avoiding collected sample being blown out by the gas stream. The apparatus can further provide for withdrawing the collected sample from the conduit, if desired, without substantial loss of the sample even when the gas stream is flowing at a relatively high velocity. This is accomplished by shielding the opening of the receptacle from the gas stream as the receptacle is being withdrawn from the conduit so that the collected sample is substantially avoided from being blown out of the receptacle.

The invention is also a method of collecting a sample of particulate matter conveyed in a conduit by a gas stream comprising three steps. The first step is to insert the distal end of a sampling probe through an aperture in the conduit wall to a selected inserted position under a foreshortened duct-shaped collector element, the sampling probe having adjacent the distal end a receptacle portion with a cup-like cavity. The cavity is oriented to face upstream to the gas flow within the conduit. The collector element is positioned above the opening of the cavity and substantially aligned therewith and having about the same interior transverse dimensions as the cavity so as to lead particulate matter into the cavity while substantially avoiding collected sample from being blown out of the cavity by the gas stream during sample collection within the conduit. The second step is to retract the distal end of the sampling probe to bring the cavity outside the conduit. The third step is to shield the opening of the cavity during the step of retracting the sampling probe so as to substantially avoid collected sample from being blown out of the cavity by the gas stream as the cavity is removed from under the collector element. The sample now being outside the conduit, it can be, for example, subjected to chemical or physical anaysis such as the determination of moisture content or the determination of particle size.

BRIEF DESCRIPTION OF THE DRAWINGS

FIG. 1 shows a side view partly in full and partly in cross-section of a preferred embodiment of the invention for collecting and withdrawing a particulate sample from a conduit with the sample receptacle in the inserted position within the conduit.

FIG. 2 shows a top view, mostly in full and partly in setion, of the embodiment shown in FIG. 1.

FIG. 3 shows a side view partly in full and partly in cross-section of a preferred embodiment of the invention for collecting and withdrawing a particulate sample from a conduit with the sample receptacle in the retracted position.

FIG. 4 shows a full top view of a preferred embodiment of the invention for collecting and withdrawing a particulate sample from a conduit and in a form readily mountable to a round conduit.

FIG. 5 shows a cross-sectional side view of a preferred embodiment of the invention for collecting a particulate sample from a conduit with the sample receptacle permanently positioned within the conduit.

DETAILED DESCRIPTION OF THE INVENTION

For the purposes of understanding the principles of the invention, reference will now be made to the embodiments illustrated in the drawings and specific language will be used to describe the same. Since many changes and variations of the disclosed embodiment may be made without departing from the inventive concept, it is not intended to limit the scope of the appended claims.

Referring to the drawings, FIG. 2 shows a top view, mostly in full and partly in section, of a preferred sampler 10 mounted on a conduit 11. the sampler 10 is fitted to the conduit 11 by means of a flange 12. The flange 12 is welded to the conduit 11 becoming an integral portion of the conduit 11. FIG. 1 shows a cross-sectional side view of the sampler 10 and the conduit 11. The conduit 11 is shown in FIG. 2 as round but can be any shape such as oval, square or rectangular. Referring to FIG. 1, a sampling probe 13 is shown which extends through an aperture 14 in the flange 12. The probe 13 comprises a sample collection receptacle defining a cup-like cavity 15 near the end of the probe 13 which is within the conduit 11. An apertured-plate 16 is attached to the flange 12. An end-plate 23 is connected to the apertured-plate 16 by upper rods 17 and lower rods 18 held securely by threaded nuts 19. The upper rods 17 pass through bore holes 20 in the probe 13. The apertured plate 16 contains a gland that is packed with three apertured sheets of fabric reinforced rubber gasket material 22. A pneumatic actuator 25 is mounted to the end plate 23 by nut 26 and the cylinder rod 24 of the actuator 25 is connected to the probe 13 and locked thereto by a nut 27. Positioned over the cavity 15 is a foreshortened hollow duct-shaped collector element 28. The collector 28 is shown in the shape of a rectangular duct but could be round, oval, square, bell-shaped, cone-shaped or another shape to meet specific needs. The collector element 28 is attached to the flange 12 by a shield 29. When compressed air is directed into port 30 of the actuator 25, a piston 32 is driven to the right as is the piston rod 24 and the probe 13. FIG. 3 shows the probe 13 of the sampler 10 in the extreme right position with the cavity 15 shown withdrawn from the conduit 11.

In operation, the probe 13 is inserted into the conduit 11 by directing compressed air into the second port 31 of actuator 25 as shown in FIG. 1 and in FIG. 2. Particulate matter pneumatically conveyed in the conduit in the direction of the arrow 33 enters the collector 28 and settles into the cavity 13 because the collector 28 tends to still the movement of gas within it. The collector 28 substantially prevents particulate material collected in the cavity 13 from being blown out of the cavity 13 by gas stream in the conduit and especially when the gas stream is flowing at a relatively high average velocity such as about 80 feet per minute, i.e., the bottom of the cavity 15 is at least covered with particulate material. The transverse interior dimensions of the collector element 28 are not critical as long as they are about the same as the cavity 15, e.g., if the exterior dimensions of the collector element are substantially less than the cavity then collected particulate matter can be blown out of the cavity to such an extent that the bottom of the cavity 15 is not at least covered with sample. The height of the collector 28 is not critical in the invention but generally needs to be higher for higher velocity gas flow in the conduit 11. A gap 34 between the collector 28 and the probe 13 is necessary to allow relative movement between the two. When the walls of the collector 28 and the cavity 15 are not parallel, then the transverse interior dimensions of the collector 28 and the cavity 15 should be about the same at the gap 34. Preferably, the gap 34 is as small as practical and generally smaller than the particle size of the particulate material being conveyed in the conduit 11 to prevent the loss of sample through the gap 34. However, some loss of sample through the gap 34 can be tolerated and again the only critical criteria is that the bottom of the cavity 15 be at least covered with sample, i.e., an excessive gap 34 is believed to prevent sample from settling in the cavity 15 or allow collected sample to be blown out of the cavity 15 even when the transverse dimensions of the collector 28 and the cavity 15 are about the same.

When compressed air is directed to the first port 30 of the actuator 25, the probe 13 and the cavity 15 are withdrawn from the conduit 11 as shown in FIG. 3. Several problems can occur as the cavity 15 is being withdrawn from the conduit 11. The first problem is sample being blown from the cavity 15 as the cavity 15 begins to be withdrawn and is no longer in alignment with the collector 28. A means for shielding the cavity 15, in this event, is shown in FIGS. 1, 2, and 3 as the shield 29 which is a strip of substantially rigid sheet-like material; one end of which is supported by and held by attachment means to the flange 12 and the other end of which is attached to and supports the collector 28. If the shield 29 is not rigid enough, it will be blown downwards and interfere with the probe 13, especially if the shield is blown downwards when the probe 13 is in its retracted position. The projected area of the shield 29 substantially overlaps the opening of the cavity 15 as it is withdrawn from the conduit. The shield 29 is a preferred embodiment but other means are contemplated to be effective as well such as jets of air directed across the top of the cavity 15 as it is withdrawn or a cover slid over the opening of the cavity 15 before it is withdrawn. The second problem that can occur as the cavity 15 is being withdrawn is the condition when the cavity 15 is aligned with the gaskets 22. Then there can be an open path between the interior and the exterior of the conduit 11. To prevent this problem a lip 35 is provided on the apertured plate 16 to block the opening of the cavity 15 as the probe 13 is being withdrawn.

The gaskets 22 are preferably fabric reinforced rubber but it is believed that many other resilient gasket materials should work. The function of the gaskets is to seal the probe and prevent leaks of gas from the interior to the exterior of the conduit 11. The seals tend to deteriorate in use if the particulate solid conveyed in the conduit 11 abrades the gasket. The preferable use of multiple gaskets, i.e., 3 gaskets, extends the life time of effective sealing. A preferred material of construction for the probe 13, the plate 16 and the plate 23 is aluminum because of its ease of machining. A preferred material of construction for the rods 17 and 18, the flange 12, the collector 28 and the shield 29 is steel because of its strength.

When the probe 13 is at the position shown in FIG. 3, the sample in the cavity 15 is available for use, e.g., a near-infrared analyzer, not shown, can be mounted above the cavity 15 so that the moisture content of the sample in the cavity 15 can be determined. The sample in the cavity 15 can be returned to the conduit 11 by reinserting the probe as shown in FIG. 1 and then directing compressed air to channel 36 of the probe 13. The channel 36 terminates as a slot in the cavity 15 and the compressed air blows the sample out of the cavity 15 and into the conduit 11. The compressed air is then turned off and another sample collected.

Referring to FIG. 4, therein, is shown the sampler 10 and the flange 12 in a form readily mounted to a round conduit. The shape and dimensions of the flange 12 would be altered to mount the sampler 10 to other shape conduits such as a rectangular conduit or an oval conduit.

Referring to FIG. 5, therein, is shown an embodiment of the invention having a non-movable probe 13a mounted in a conduit 11a. The collector element 28a is shown in the shape as a frustro cone attached to the conduit 11a by a bracket 37. It is contemplated that a collector shaped like the collector 28a would be less likely to plug with particulate matter especially when used in the embodiment of the invention shown in FIG. 1. No shield is used in the embodiment, shown in FIG. 5, because the probe 13a is non-movable during normal use. The sample collection cavity 15a is shown in circular form. The shape of cavity 15a is not critical as long as the collector 28a is positioned adjacent the opening of the cavity 15a and substantially aligned therewith and having about the same transverse dimensions for the same reasons as mentioned above in regard to the embodiment of the invention shown in FIG. 1.

The embodiment of the invention shown in FIG. 5 is contemplated to be applicable to, for example, analysis of certain collected samples, conveyed in the direction of the arrow 33a, within the conduit 11a for moisture content by the established chemical analysis technique of neutron absorption. A neutron radiation source 38 on one side of the cavity 15a could direct a beam of neutrons across the cavity 15a to a neutron detector 39. In operation, the cavity 15a would fill with sample and its moisture content would be determined by the neutron absorption technique. Then compressed air would be directed to the channel 36a to blow the sample from the cavity 15a. The cycle of analysis would be repeated by turning off the flow of compressed air to the channel 36a and again allowing sample to collect in the cavity 15a.

What is claimed is:

1. A sampling apparatus for collecting a sample of particulate matter conveyed in a conduit by a gas stream, comprising:
    a sampling collection receptacle defining a cup-like cavity with the opening thereof adapted to be oriented to face upstream to the flow of gas within the conduit; and
    a foreshortened hollow duct-shaped collector element positioned adjacent the opening of the cavity and substantially aligned therewith and having about the same interior transverse dimensions as the cavity so that collected sample is substantially kept from being blown out of the cavity by the gas stream during sample collection within the conduit.

2. The apparatus of claim 1 wherein the receptacle is a portion of a retractable sampling probe, the receptacle being adjacent an end of the probe.

3. The apparatus of claim 2 further including at least a portion of the conduit, the conduit portion having an aperture in the wall thereof through which the receptacle portion of the sampling probe slidably extends and further including means for periodically inserting and subsequently retracting the receptacle portion of the sampling probe through the aperture.

4. The apparatus of claim 3 wherein the means for inserting and retracting the sampling probe includes a pneumatic actuator adapted to controllably reciprocate the sampling probe.

5. The apparatus of claim 3 further including means for shielding the opening of the cavity while the sampling probe is being retracted from the conduit so that collected sample is substantially kept from being blown out of the cavity by the stream during retraction of the sampling probe through the aperture.

6. The apparatus of claim 5 wherein the means for shielding is a strip of substantially rigid sheet-like material, one end of which is supported and held by attachment means to the conduit portion, the other end of which is to and supports the collector element, the thereby projected area of the strip substantially overlapping the opening of the cavity as the sampling probe is being retracted.

7. The apparatus of claim 3, further comprising resilient gasket means substantially sealing any annular space between the sampling probe and the aperture, the gasket means providing for a slidable relationship with the sampling probe.

8. The apparatus of claim 1 further comprising means for blowing collected sample out of the cavity.

9. The apparatus of claim 8 wherein the means for blowing collected sample out of the cavity comprises a slot in the wall of the receptacle through which a jet of gas is introduced into the cavity.

10. A method of collecting a sample of particulate matter conveyed in a conduit by a gas stream, comprising the steps of:
    inserting a distal end of a sampling probe through an aperture in the conduit wall to a selected inserted position under a foreshortened hollow duct-shaped collector element, the sampling probe having adjacent the distal end a receptacle portion defining a cup-like cavity, the cavity being oriented, upon insertion of the distal end of the sampling probe to the selected position, to face upstream to the gas flow within the conduit, the collector element positioned above the opening of the cavity and substantially aligned therewith and having about the same interior transverse dimensions as the cavity so as to lead particulate matter into the cavity while substantially keeping collected sample from being blown out by the gas stream during sample collection within the conduit;
    retracting the distal end of the sampling probe, thereby bringing the cavity outside the conduit; and
    shielding the opening of the cavity during the retracting step so as to substantially keep collected sample from being blown out of the cavity by the gas stream as the cavity is retracted from under the collector element.

11. The method of claim 10 wherein the shielding used is a substantially rigid sheet-like material having two ends, one end of which is supported by and held by attachment means to the wall of the conduit, the other end of which is attached to and supports the collector element, the projected area of the strip substantially overlapping the opening of the cavity during the retracting step.

* * * * *

UNITED STATES PATENT AND TRADEMARK OFFICE
CERTIFICATE OF CORRECTION

PATENT NO. : 4,771,642

DATED : Sep. 20, 1988

INVENTOR(S) : William H. Parth; Charles J. Myers

It is certified that error appears in the above-identified patent and that said Letters Patent is hereby corrected as shown below:

```
Col. 2, line 44, delete "anaysis" and insert --analysis--;
        line 54, delete "setion" and insert --section--.

Col. 3, line 14, delete "the" and insert --The--.

Col. 6, Claim 5, line 11, after "the", second occurrence,
                          insert --gas--;

Claim 6, line 17, after "is" insert --attached--;

Claim 10, line 39, delete "oollector" and insert
                          --collector--.
```

Signed and Sealed this

Eighteenth Day of July, 1989

Attest:

DONALD J. QUIGG

*Attesting Officer*        *Commissioner of Patents and Trademarks*